US010586069B2

(12) United States Patent
Shah

(10) Patent No.: US 10,586,069 B2
(45) Date of Patent: Mar. 10, 2020

(54) NETWORKING DEVICES FOR STORING PROFILES LONGITUDINALLY

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 961 days.

(21) Appl. No.: 15/163,667

(22) Filed: May 24, 2016

(65) Prior Publication Data
US 2017/0344702 A1 Nov. 30, 2017

(51) Int. Cl.
*G06F 16/30* (2019.01)
*G06F 7/00* (2006.01)
*G06F 21/62* (2013.01)
*G16H 10/60* (2018.01)
*G06F 19/00* (2018.01)

(52) U.S. Cl.
CPC .......... *G06F 21/6245* (2013.01); *G06F 19/00* (2013.01); *G06F 21/6227* (2013.01); *G16H 10/60* (2018.01)

(58) Field of Classification Search
CPC .. G06F 21/6245; G06F 21/6227; G06F 19/00; G16H 10/60
USPC ........................................................ 707/733
See application file for complete search history.

(56) References Cited

U.S. PATENT DOCUMENTS

| 6,035,276 | A | 3/2000 | Newman et al. | |
| 7,325,202 | B2 | 1/2008 | Shirriff | |
| 7,467,113 | B2* | 12/2008 | McFarlin | G06Q 20/401 |
| | | | | 705/59 |
| 2002/0082876 | A1* | 6/2002 | Martin | G06Q 40/02 |
| | | | | 705/4 |
| 2002/0161605 | A1* | 10/2002 | Newman | G06F 19/328 |
| | | | | 705/2 |
| 2006/0161353 | A1* | 7/2006 | Mascarenhas | G06F 19/324 |
| | | | | 702/19 |
| 2006/0161456 | A1* | 7/2006 | Baker | G06Q 50/22 |
| | | | | 705/2 |
| 2007/0185732 | A1* | 8/2007 | Hicks | G06F 19/324 |
| | | | | 705/2 |
| 2008/0065701 | A1 | 3/2008 | Lindstrom et al. | |

(Continued)

*Primary Examiner* — Kuen S Lu
(74) *Attorney, Agent, or Firm* — Rahman LLC

(57) ABSTRACT

A method and networking device for tracking change in a computer executable profile includes retrieving computer executable profile information. The method and device may include staging the computer executable profile information in cloud staging repositories. The method and device may include splitting the computer executable profile information into constituent data types. The method and device may include defining a plurality of computer executable profile fields and corresponding profile information components. The method and device may include storing the computer executable profile information as initial computer executable profile information in a database. The method and device may include retrieving second computer executable profile information at a later time. The method and device may include mapping the initial computer executable profile information with the second computer executable profile information to identify changes.

15 Claims, 10 Drawing Sheets

(56) References Cited

U.S. PATENT DOCUMENTS

| | | | |
|---|---|---|---|
| 2010/0228564 A1 | 9/2010 | Kharraz Tavakol et al. | |
| 2012/0260209 A1* | 10/2012 | Stibel | G06Q 40/02 |
| | | | 715/780 |
| 2014/0173417 A1 | 6/2014 | He | |
| 2015/0074033 A1* | 3/2015 | Shah | G06N 5/02 |
| | | | 706/46 |

* cited by examiner

NETWORKING DEVICES FOR STORING PROFILES LONGITUDINALLY

BACKGROUND

Technical Field

The embodiments herein generally relate to networking devices, and more particularly to networking devices for tracking, storing, and credentialing of web-based profiles.

Description of the Related Art

Different web-based profile platforms provide profiles of users in accordance with information they aggregate from a variety of sources. The authenticity and reliability of the information they aggregate is however not established as they just aggregate the information and display it under profile sections of the user. In case of healthcare setup, however, there is a major problem with such information due to lack of credibility and trustworthiness. If an agency, for example, wants to run a clinical trial and use a clinician represented through such a profile as a principal investigator for a trial, figuring out what he knows, who he is, is he a fraudster or is he really a good clinician, is a major problem because of the way credentialing is done today.

In view of the above, there is a need to provide an improved networking device of profiles and management of credentialing information of the profiles.

SUMMARY

An embodiment herein provides a computer-implemented method for tracking change in a computer executable profile associated with a registered clinician. The method may include retrieving, by a processing circuit, computer executable profile information for the registered clinician, wherein the computer executable profile information includes computer executable user personal information, computer executable review information, and computer executable aggregated credentialing information obtained based on individual credentialing information components retrieved from a plurality of credentialing information sources. The method may include staging the computer executable profile information in one or more cloud staging repositories. The method may include splitting the computer executable profile information into constituent data types. The method may include defining, by the processing circuit, a plurality of computer executable profile fields and corresponding profile information components for each of the plurality of computer executable profile fields. The method may include storing the computer executable profile information including the computer executable profile fields and the corresponding profile information components as initial computer executable profile information in a database communicatively connected with the processing circuit. The method may include accessing the plurality of credentialing information sources after a defined interval of time to obtain the individual credentialing information components as indicated at a later time. The method may include retrieving second computer executable profile information based on the obtained individual credentialing information components from the plurality of credentialing information sources as indicated at the later time. The method may include mapping the initial computer executable profile information with the second computer executable profile information to identify changes in the profile information components corresponding to the computer executable profile fields, wherein the changes are indicative of reliability of credentialing of the profile over time. The method may include defining a set of computer executable notification rules to selectively generate notifications corresponding to the changes between the initial computer executable profile information and the second computer executable profile information upon identification of such changes and generate notifications corresponding to the changes between the initial computer executable profile information and the second computer executable profile information over a defined time period as and when requested by a user computer, communicatively connected with the processing circuit, through a search query submitted to the processing circuit. The method may include determining a crowdsourced credentialing index for the profile based on the changes over time obtained from the mapping of the initial computer executable profile information and the second computer executable profile information. The method may include generating an electric signal comprising data signifying the changes in the profile information. The method may include transmitting the electric signal from the processing circuit, in a network comprising a plurality of communicatively linked data communication devices. The method may include converting the electric signal into a plurality of pixels. The method may include displaying the plurality of pixels on a display unit to indicate timeline views of the second profile information and the changes based on the computer executable notification rules.

An embodiment herein provides a computer-controlled system for tracking change in a computer executable clinician profile. The system may include a plurality of cloud staging repositories to store computer executable profile information as obtained from a plurality of information sources in unstructured form. The system may include a database for storing structured initial computer executable profile information, wherein the structured initial computer executable profile information includes computer executable clinician personal information, computer executable review information, and computer executable aggregated credentialing information. The computer executable profile information is aggregated from the plurality of information sources comprising a plurality of credentialing information sources such that the computer executable aggregated credentialing information is generated based on individual credentialing information components retrieved from the plurality of credentialing information sources. The database further stores a set of computer executable notification rules to selectively (1) generate default notifications corresponding to changes in the structured initial computer executable profile information upon identification of such changes and (2) generate notifications corresponding to the changes in the structured initial computer executable profile information over a defined time period as and when requested by an external computer through a search query. The system may include a processing circuit to split the computer executable profile information into constituent data types, define a plurality of computer executable profile fields and corresponding profile information components for each of the plurality of computer executable profile fields, and access the plurality of credentialing information sources after a defined interval of time to obtain the individual credentialing information components as indicated at a later time. The processing circuit further generates structured second computer executable profile information based on the obtained individual credentialing information components from the plurality of credentialing information sources as indicated at the later time. The processing circuit maps the structured initial computer executable profile information with the structured second computer executable profile information to identify the changes in the profile information components corresponding to the computer executable profile fields, wherein the changes are indicative of a change in reliability of credentialing of the computer executable clinician profile over time. The processing circuit executes the set of computer executable notification rules to generate the notifications. The processing circuit determines a crowd-sourced credentialing index for the clinician profile based on the changes over time obtained from the mapping of the structured initial computer executable profile information and the structured second computer executable profile information. The processing circuit generates an electric signal comprising data signifying the structured second computer executable profile information and changes in the structured initial computer executable profile information, transmits the electric signal, in a network comprising a plurality of communicatively linked data communication devices, convert the electric signal into a plurality of pixels, and displays or causes to display the plurality of pixels on a display unit to indicate timeline views of the structured initial computer executable profile information and the changes based on the computer executable notification rules.

BRIEF DESCRIPTION OF THE DRAWINGS

In the drawings, like numerals describe similar components substantially throughout the several views. The drawings illustrate generally, by way of an example, but not by a way of limitation, various embodiments.

DETAILED DESCRIPTION

Figure 1:
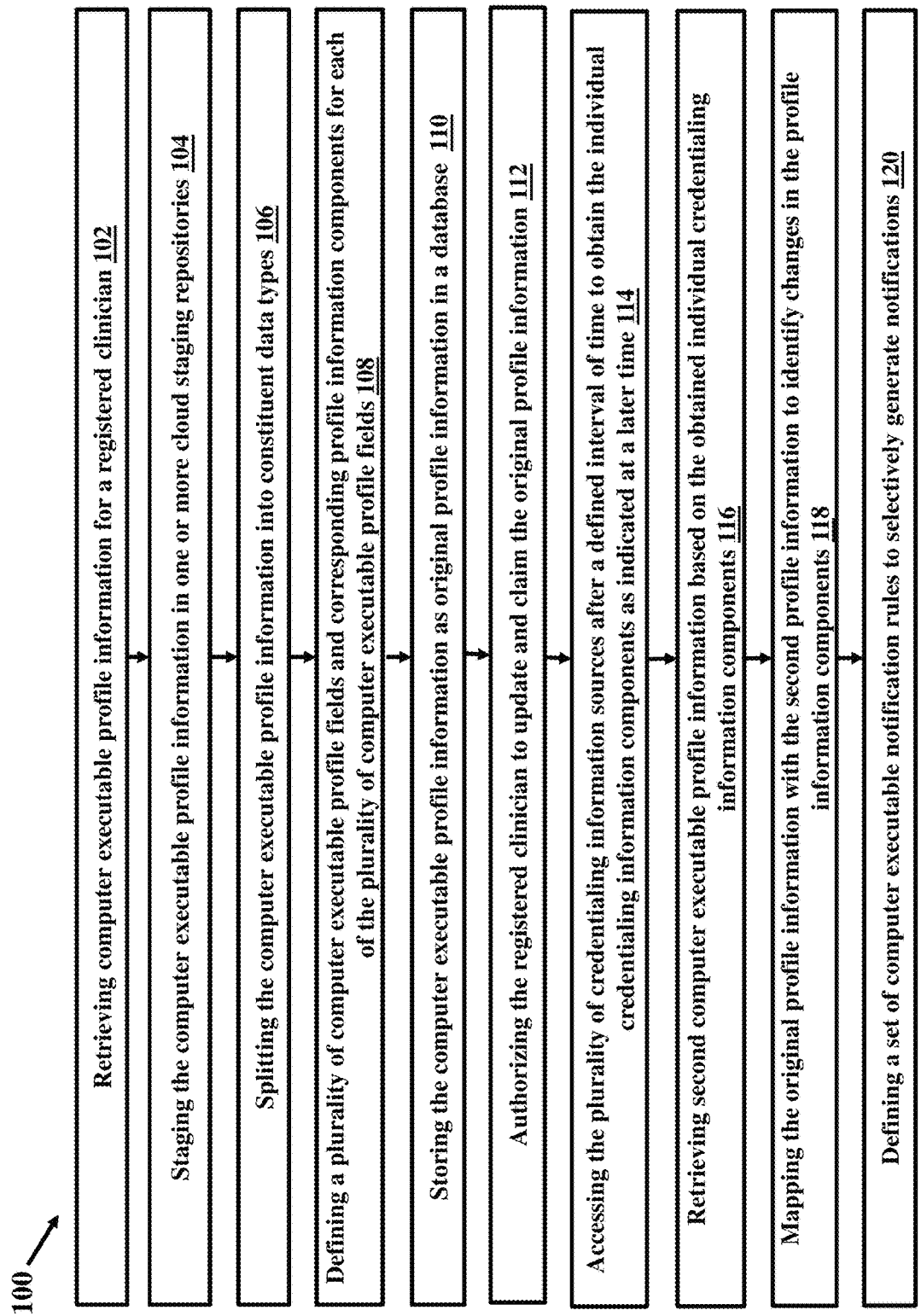
FIG. 1 illustrates a flow diagram of a method for tracking change in a computer executable profile associated with a registered clinician in accordance with an embodiment herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated. Referring now to the drawings, and more particularly to FIGS. 1 through 10, where similar reference characters denote corresponding features consistently throughout the figures, there are shown preferred embodiments.

FIG. 1 illustrates a flow diagram of a method 100 for tracking change in a computer executable profile associated with a registered clinician in accordance with an embodiment herein. The method 100 may include retrieving computer executable profile information for the registered clinician from a variety of information sources, at step 102. The information sources may include such as but not limited to social network websites, hospitals, institutes, clinics, individual websites of healthcare providers, electronic medical repositories, heath record systems, clinical data sources, health information exchange systems, bio informatics systems, and the like. The registered clinician may be a physician, clinician, medical professional, healthcare provider, health support professional, or any other person who is registered with a web-based interface of a service platform enabled with the use of the teachings recited in the document herein. While the embodiments herein may be discussed with reference to clinicians or physicians or other healthcare professionals interchangeably without limitations, it must be however appreciated by a person ordinarily skilled in the art that the embodiments may be applicable to other professionals without deviating from scope and spirit of the embodiments herein.

The computer executable profile information may include computer executable user personal information. The computer executable user personal information may include such as without limitations first name of the clinician, last name of the clinician, medical specialty, treatment information, training, awards, criminal background checks, and litigation information associated with the clinician such as pending lawsuits, cases filed against the clinician etc.

The computer executable profile information may include computer executable review information. The computer executable review information may include such as without limitations patient reviews and peer reviews. For example, the patient reviews may include such as without limitations bedside manner, waiting time, level of patient comfort, communication, professionalism, or any other feedback or comments from patients to the clinician in an embodiment. Peer reviews in an example may include such as without limitations details or comments from other doctors or clinicians that are indicative of what other doctors or healthcare professionals are saying about the registered clinician. The review information may further include computer executable information indicative of comparison of clinicians (in terms of such as procedure, success, number, cost and the like) that may be derived directly from peers or patients or may be calculated based on computer executable inputs provided by the patients or peers.

The computer executable profile information may further include computer executable aggregated credentialing information. The computer executable aggregated credentialing information is obtained based on individual credentialing information components retrieved from a plurality of credentialing information sources 402 as discussed later in conjunction with FIG. 4.

The method 100 may further include staging the computer executable profile information in one or more cloud staging repositories, at step 104. The cloud staging repositories may store the computer executable profile information as is in raw data form. In an example, the computer executable profile information may be ingested from the information sources into the cloud staging repositories continuously in a streamed manner. In an example, the computer executable profile information may be ingested into the cloud staging repositories in a batch manner. In an example, the computer executable profile information may be ingested into the cloud staging repositories upon triggering of an event.

The method 100 may further include splitting the computer executable profile information into constituent data types, at step 106. The different data types may be defined such as clinician first name, clinician last name, education, treatment, training, medical specialty, litigation and the like without limitations in view of various profile aspects as discussed above.

The method 100 may further include defining a plurality of computer executable profile fields (also referred to as profile fields or computer executable profile fields interchangeably without limitations merely for simplicity of description) and corresponding profile information components for each of the plurality of computer executable profile fields, at step 108. For example, the profile fields for 'clinician' name may include first name, last name, and middle name. Similarly, profile fields for 'education' may include such as graduation, post-graduation, doctorate, and the like. Similarly, profile fields may be defined for several or all of the data types as identified after the splitting step. Once, the profile fields are defined, respective information for the clinician may be obtained from the split data types and defined as the corresponding profile information components against each of the profile fields. For example, the 'first name' of a clinician may be a field and the actual first name of the clinician (which may be identified from the split data types) may be its corresponding profile information component for the clinician. For any other clinician, corresponding profile information components may be different. Also, in some embodiments, the profile fields may also be different for different clinicians. For example, a clinician specialized in cancer surgery may require certain profile fields while another clinician specialized in brain surgery may require at least one different field in order to capture the computer executable profile information properly and completely. Similarly, clinicians located at different geographies may require at least one different clinician specific profile field in order to capture the computer executable profile information. However, in some embodiments, the profile fields may not vary and a generalized template may be used for all clinicians. The computer executable profile information obtained after splitting into the data types and structuring according to the profile fields may be referred to as structured computer executable profile information.

At step 110, the method 100 may further include storing the structured computer executable profile information as 'initial structured computer executable profile information' in a database. The 'initial structured computer executable profile information' is associated with a specific time instance to represent status of the profile information at a particular instant of time indicative of an initial time instance when the computer executable profile information is collected for the first time.

At step, 112, in some embodiments, the method 100 may include authorizing the registered clinician to update and/or claim the 'initial structured computer executable profile information'. In an example, the clinician may be sent an invite to registered email address for authorizing access to the 'initial structured computer executable profile information'. The clinician may be allowed to access the 'initial structured computer executable profile information' by confirming the registered email address through one of several ways including but not limited to a single sign-in scheme enabled through the registered email address. In an example, the single sign-in scheme may be enabled through a social networking engine for accessing a socially aware network. The single sign-in scheme may allow the clinician to access the 'initial structured computer executable profile information' and make any edits or updates in the 'initial structured computer executable profile information'. In an example, the clinician may be allowed to claim the 'initial structured computer executable profile information' such that the claimed profile information may be recognized as more authentic than any non-claimed profile information.

In an embodiment, the term single sign-on scheme herein means that a clinician provides a single unique identifier (ID) and password combination (also referred to as credential information or login details or login credential) to gain access to one or multiple sources of a database over a communication network such as the Internet. In an embodiment, the term single sign-on scheme is defined such that a clinician may provide any of several unique identifiers (IDs) and password combinations associated with several distinct social networking services respectively to gain access to one or multiple services disclose herein.

In an example, a new unregistered clinician (who is not yet registered) may request for an addition of her profile. The new unregistered clinician may send a request for profile incorporation along with minimum necessary details. The unregistered clinician may then be registered upon acceptance of the incorporation request and then steps 102-110 and 114-120 may be implemented in a manner similar to other registered clinician.

At step 114, the method may further include accessing the plurality of credentialing information sources after a defined interval of time to obtain the individual credentialing information components as indicated at a later time. In an example, one or more of the plurality of credentialing information sources may provide the individual credentialing information components to the registered clinician and influence credibility and/or reputation and/or trust score of the clinician. As will be discussed further later, the individual credentialing information components obtained from the credentialing information sources may be aggregated to generate aggregated credentialing information. The credentialing information sources may include without limitations hospital, government agency, healthcare institute, university, medical center and the like.

The method 100 may further include, at step 116, retrieving second computer executable profile information based on the obtained individual credentialing information components or the aggregated credentialing information retrieved after the defined interval of time. The defined interval of time or time gap between successive retrievals of the individual credentialing information components or the aggregated credentialing information may be predefined or may be varied based on requirements or may be defined to follow specific rules. In an example, the time gap may be one year or one month of one week or varies progressively in a defined pattern or without any pattern but following specific rules or varies in accordance with a triggering event. The second computer executable profile information may be structured in a manner similar to the initial computer executable profile information to generate a 'structured second computer executable profile information'.

The 'structured second computer executable profile information' is associated with a specific time instance to represent status of the computer executable profile information after the defined interval of time. The 'structured second computer executable profile information' is indicative of an evolved profile status and reflects an updated profile status of the registered profile or the registered clinician. In an embodiment, the 'initial computer executable profile information' and the 'second computer executable profile information' may represent time variants or time-dependent versions of the computer executable profile information associated with the registered profile of the clinician or the registered clinician. In an embodiment, the 'structured initial computer executable profile information' and the 'structured second computer executable profile information' may represent post structuring versions of the 'initial computer executable profile information' and the 'second computer executable profile information' associated with the registered profile of the clinician or the registered clinician.

At step 118, the method 100 may further include mapping the 'structured initial computer executable profile information' with the 'structured second computer executable profile information' to identify changes in the profile information components corresponding to the computer executable profile fields. For example, the mapping may compare the information components field by field for each of the 'structured initial computer executable profile information' and 'structured second computer executable profile information'. The mapping may identify if there are any changes in any of the fields and also the information components across one or more fields corresponding to which the changes are identified. For example, the step of mapping may compare a credentialing information component of the 'structured initial computer executable profile information' with a corresponding credentialing component of the 'structured second computer executable profile information'. In an example, the changes are indicative of reliability of credentialing of the computer executable profile information over time. In an example, the changes may occur in the computer executable user personal information or computer executable review information or any other portion of the computer executable profile information.

At step 120, the method 100 may include defining a set of computer executable notification rules to generate notifications selectively using one of two modes as discussed hereafter.

In an example, the notification rules may be defined so as to generate alerts or notifications corresponding to the changes between the 'structured initial computer executable profile information' and the 'structured second computer executable profile information' as soon as the changes are identified upon mapping. For example, if after the mapping step any changes are identified, the alerts and notifications may be generated immediately. In an example, the alerts and notifications may be sent to concerned authorities. The concerned authorities may for example be registered entities such as insurance agents, clinical trial agencies and the like who may need to know how do credentials or other profile components change over time.

In an example, the notification rules may be defined so as to generate the alerts or notifications corresponding to the changes between the 'structured initial computer executable profile information' and the 'structured second computer executable profile information' over a period of time as and when requested by an external computer associated with the concerned authorities. The external computer may be communicatively connected with a processing circuit executing the notifications rules through a search query submitted to the processing circuit. For example, a concerned authority may submit a query requesting changes in the 'structured initial computer executable profile information' and the 'structured second computer executable profile information' over a defined period of time such as over the last year. The processing circuit may then generate the notifications and send a computer executable file containing the changes for the defined period of time or for the last one year as requested.

In an embodiment, the alerts or notifications may be generated to indicate a clinician fraud when the changes are identified in the computer executable profile information components corresponding to any of the computer executable profile fields. In an example, the alert or notifications may be generated to indicate clinician fraud when the changes are identified in the profile fields corresponding to the individual credentialing information components so that the changes are indicative of only crowdsourced credentialing reliability and trust.

In accordance with the embodiments discussed herein, the notifications rules may be defined differently to allow the concerned authority to either receive the notifications for the changes as soon as such changes happen or to receive the notifications only when needed and for specific types of changes or only when some specific changes happen.

In an example, the changes may be indicative of reliability of credentialing of the computer executable profile information over time since only the plurality of credentialing information sources are accessed at the later time and the individual credentialing components are retrieved as indicated at the later time for tracking the changes in the computer executable profile information. Therefore, the changes in the 'structured initial computer executable profile information' and the 'structured second computer executable profile information' are only due to the newly identified credentialing information components at the later time.

The method 100 may also include determining a crowdsourced credentialing index for a 'structured computer executable profile information' such as the 'structured initial computer executable profile information' or the 'structured second computer executable profile information' or any other time variant version of the 'structured initial computer executable profile information' based on the changes over time obtained from the mapping of the two or more time variant versions of the 'structured computer executable profile information'. The crowdsourced credentialing index is associated with and is indicative of reliability and trustworthiness of the computer executable profile information. The more the changes are noted between such as the 'structured initial computer executable profile information' and the 'structured second computer executable profile information', the lower is the crowdsourced credentialing index representing a lower score of reliability and trust and vice versa. In an example, the method 100 may include generating an alert indicative of a clinician fraud when the crowdsourced credentialing index drops below a defined threshold over time. For example, if the extent of changes is drastic, the crowdsourced credentialing index may drop down too low and may mark clinician fraud requiring urgent attention.

The method 100 may also include generating an electric signal comprising data signifying the changes between the 'structured initial computer executable profile information' and the 'structured second computer executable profile information'. The signal may be transmitted from the processing circuit (as shown in later figures), in a network comprising a plurality of communicatively linked data communication devices. The electric signal may be converted into a plurality of pixels which may be displayed on a display unit to indicate timeline views of the 'structured computer executable profile information' and the changes based on the computer executable notification rules. The timeline views are discussed further in conjunction with subsequent figures.

Figure 2:
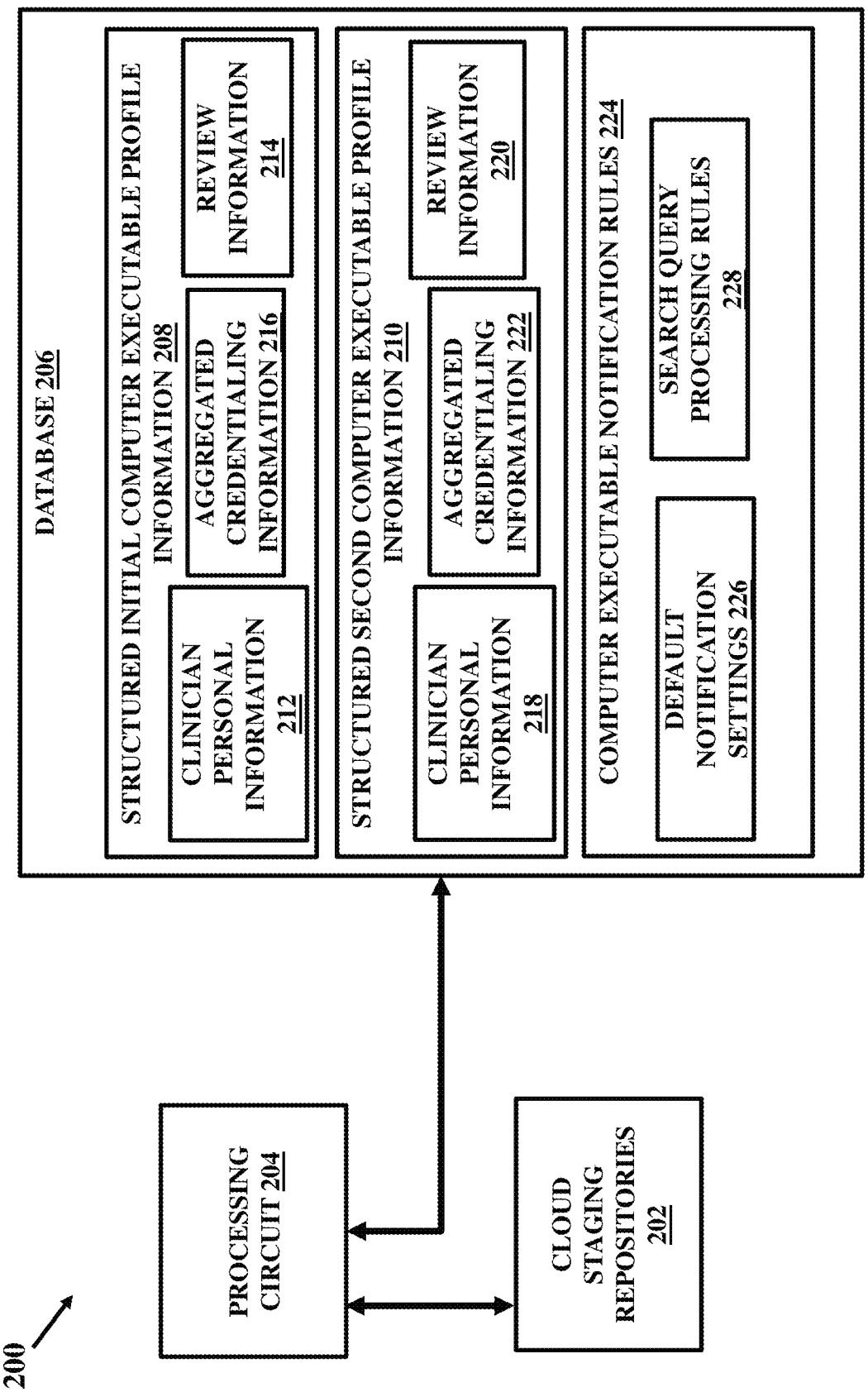
FIG. 2 illustrates a schematic diagram of a computer-controlled system for tracking change in a computer executable profile, in accordance with an embodiment herein.

FIG. 2, with reference to FIG. 1, illustrates a schematic diagram of a computer-controlled system 200 for tracking change of the computer executable clinician profile, in accordance with an embodiment herein. The system 200 includes cloud staging repositories 202, a processing circuit 204, and a database 206.

The cloud staging repositories 202 are used to store the computer executable profile information as obtained from the plurality of information sources in unstructured form or raw form. For example, discrete portions of the computer executable profile information may be obtained from different information sources which together make up the complete profile information only after structuring. The computer executable profile information that is stored in the cloud staging repositories 202 may not be processed yet or may for example contain duplicates or unnecessary or redundant information. In an example, the computer executable profile information contained in the cloud staging repositories 202 may only be present for either temporary usage or in some cases may be stored permanently but may have to be transformed before actually moving the computer executable profile information further across different forward flow points toward the database 206 and eventual publishing or display or analytics as will be discussed later.

The processing circuit 204 may be configured to perform a variety of pre-processing, post-processing and information structuring tasks such as those discussed in conjunction with FIG. 1 without limitations.

The processing circuit 204 may obtain the computer executable profile information from the cloud staging repositories 202 and split the computer executable profile information into the constituent data types. The different data types may be defined such as clinician first name, clinician last name, education, treatment, training, medical specialty, litigation and the like without limitations in view of various profile aspects as discussed above in conjunction with FIG. 1. For example, the processing circuit 204 may split the computer executable profile information into various fields and the profile information components such as clinician first name, the last name, education, litigation information, and the like without limitations. After splitting, the various profile information components may be segregated and classified under different fields.

In an embodiment, the profile fields corresponding to the profile information components may be defined by the processing circuit 204. For example, the processing circuit 204 may pre-define what fields need to be updated for a clinician category and accordingly the profile information components are identified from the computer executable profile information by splitting the computer executable profile information obtained from the cloud staging repositories 202.

The computer executable profile information is then structured by the processing circuit 204 such that the 'structured initial computer executable profile information' 208 contains the various profile information components structured according to the various pre-defined fields by the processing circuit 204.

The 'structured computer executable profile information' may be associated differently at different instances of time by the processing circuit 204. For example, the processing circuit 204 may access the plurality of credentialing information sources after some time such as after a week or a month or a year and the like to identify the credentialing information after some time. The processing circuit 204 may obtain the individual credentialing information components associated with the individual credentialing information sources as indicated at a later time. In some embodiments, the credentialing information components as identified at the later time may be similar or same as the credentialing information components identified earlier during initial computer executable profile information gathering. In some embodiments, however, the credentialing information as identified earlier and later may not match and may vary.

After accessing the credentialing information components at the later time, the processing circuit 204 may generate the structured computer executable profile information again based on the obtained individual credentialing information components from the plurality of credentialing information sources as indicated at the later time. The newly generated computer executable profile information may be referred to as the second computer executable profile information which may undergo through the same process of structuring of the information to transform the second computer executable profile information into the 'structured second computer executable profile information' 210 as discussed above in the document. As discussed earlier also in the document, the 'structured initial computer executable profile information' 208 may contain the clinician personal information 212, review information 214, and the aggregated credentialing information 216. The 'structured second computer executable profile information' 210 may contain the clinician personal information 218, review information 220, and the aggregated credentialing information 222.

The processing circuit 204 may map or compare the 'structured initial computer executable profile information' 208 with the 'structured second computer executable profile information' 210 to identify changes in the profile information components corresponding to the computer executable profile fields. The changes may be indicative of a change in reliability of credentialing of the computer executable clinician profile over time. The processing circuit 204 may further execute a set of computer executable notification rules that may be pre-defined by the processing circuit 204 to generate the alerts and notifications. The processing circuit 204 may configure notification and alerts generation selectively to generate the notifications either upon request from the external computer or automatically as and when any changes are detected by the processing circuit 204 during mapping of the 'structured initial computer executable profile information' and the 'structured second computer executable profile information'.

The processing circuit 204 may be configured to generate the electric signal comprising the data signifying the 'structured second computer executable profile information' and the changes in the 'structured initial computer executable profile information'. The processing circuit 204 may then transmit the electric signal, in a network comprising a plurality of communicatively linked data communication devices. The electric signal is then converted into a plurality of pixels by the processing circuit 204. The processing circuit 204 displays or causes another processor to display the plurality of pixels on a display unit to indicate the timeline views of the 'structured initial computer executable profile information' and the changes based on the computer executable notification rules. The timeline views are a reflection of how do the changes occur in the computer executable profile information since its original time instance and through various time occurrences such as after a week or after two weeks or after every week, or after every month or after every year and the like.

The database 206 may store the 'structured initial computer executable profile information' 208 and the 'structured second computer executable profile information' 210 after performing various processing activities on the computer executable profile information obtained from the cloud staging repositories 202. The database 206 may further store the set of computer executable notification rules 224 to selectively generate default notifications corresponding to changes in the 'structured initial computer executable profile information' 208 upon identification of such changes and generate the notifications corresponding to the changes in the 'structured initial computer executable profile information' 208 over a defined time period as and when requested by the external computer through a search query.

The database 206 may store the 'structured initial computer executable profile information' 208 which may contain the clinician personal information 212, review information 214, and the aggregated credentialing information 216 (or simply referred to as credentialing information). The database 206 may also store the 'structured second computer executable profile information' 210 which may also contain clinician personal information 218, review information 220, and the aggregated credentialing information 222 but at a different instant of time. Similarly, the database 206 may store a variety of computer executable profile information at different instances of time such that at each instant of time the computer executable profile information may contain clinician personal information, review information, and credentialing information.

As discussed above, the database 206 may store the computer executable notification rules 224. The computer executable notification rules 224 may contain default notification settings 226 and search query processing rules 228. The default notification rules 226 may facilitate default notifications upon identification of the changes automatically. The search query processing rules 228 may allow the external computer to receive the notifications for the changes only when requested by submitting the search query as discussed in conjunction with FIG. 1.

Figure 3:
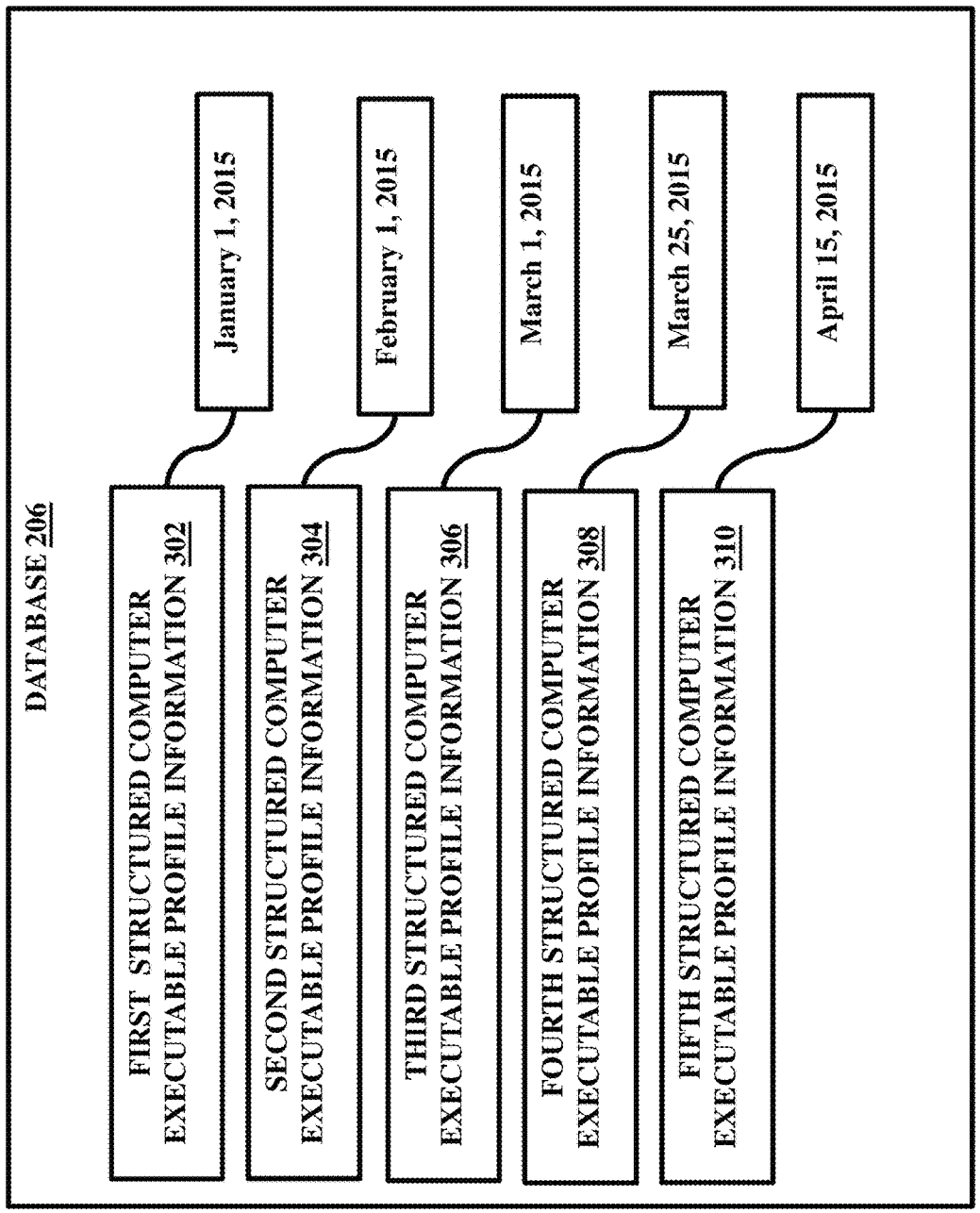
FIG. 3 illustrates exemplary structured computer executable profile information generated at different instances of time and stored in a database.

FIG. 3, with reference to FIGS. 1 and 2, illustrates exemplary structured computer executable profile information generated at different instances of time and stored in the database 206. For example, a first structured computer executable profile information 302 corresponds to the computer executable profile information generated on Jan. 1, 2015. A second structured computer executable profile information 304 corresponds to the computer executable profile information generated on Feb. 1, 2015. A third structured computer executable profile information 306 corresponds to the computer executable profile information generated on Mar. 1, 2015. A fourth structured computer executable profile information 308 corresponds to the computer executable profile information generated on Mar. 25, 2015. A fifth structured computer executable profile information 310 corresponds to the computer executable profile information generated on Apr. 15, 2015. Similarly, the computer executable profile information may be generated at various other instances of time and saved in the database 206.

Figure 4:
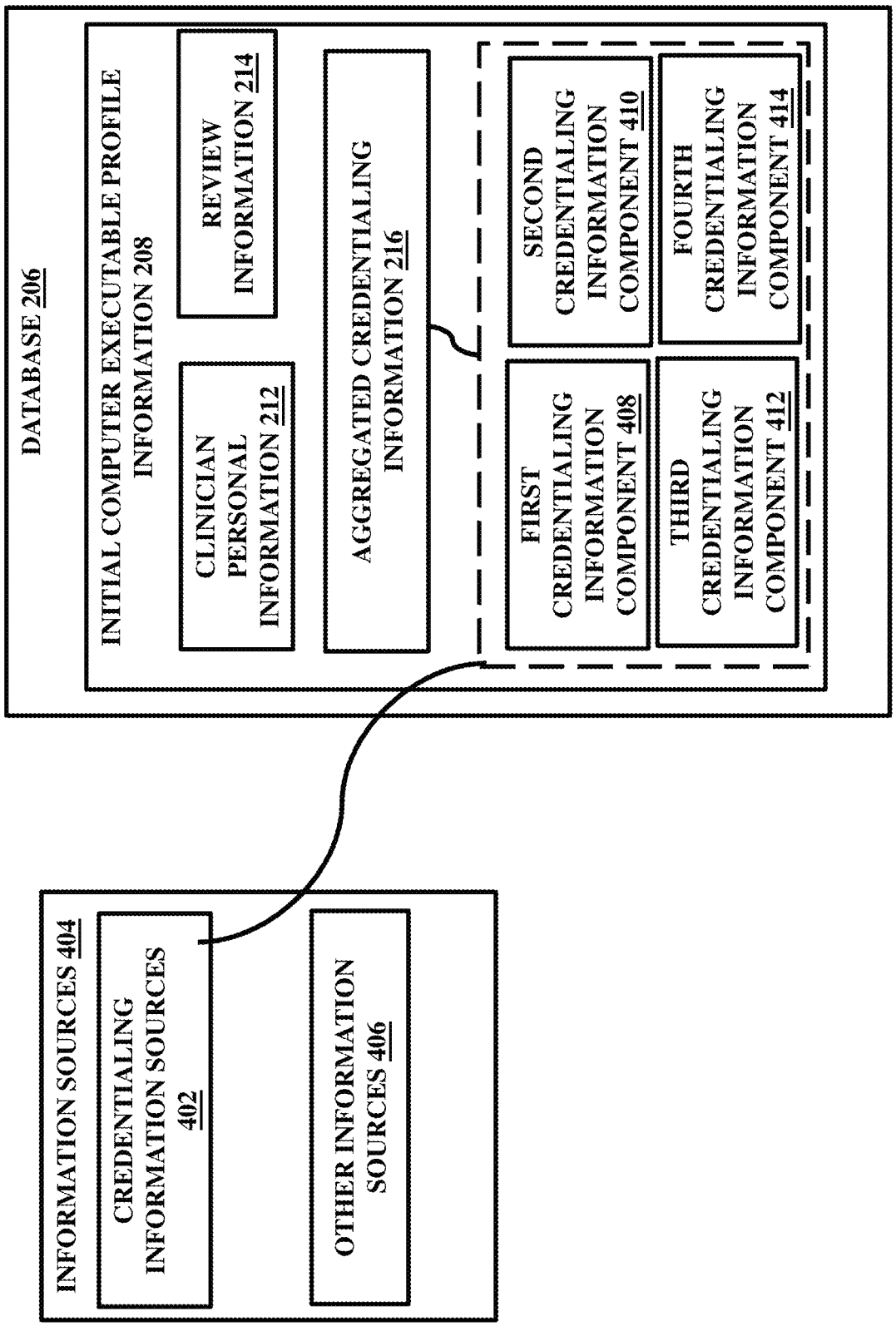
FIG. 4 illustrates organization of a computer executable profile information within a database linked to various information sources to aggregate information components, in accordance with an embodiment herein.

FIG. 4, with reference to FIGS. 1 through 3, illustrates organization of the computer executable profile information within the database 206 linked to the information sources such as information sources 404 to aggregate information components such as the credentialing information components from the remotely located credentialing information sources 402. As shown, the information sources 404 may include the credentialing information sources 402 and other information sources 406. The other information sources 406 may include such as healthcare information exchanges, electronic medical records, healthcare platforms, and the like without limitations.

The database 206 is shown to store only the 'structured initial computer executable profile information' 208 as an example. However, it must be appreciated that the database 206 may store other computer executable profile information created and maintained at different instances of time to generate a timeline view of the computer executable profile information by the processing circuit 204.

As shown, the 'structured initial computer executable profile information' includes the computer executable clinician personal information 212, computer executable review information 214, and the computer executable aggregated credentialing information 216. The computer executable aggregated credentialing information 216 includes a first credentialing information component 408, a second credentialing information component 410, a third credentialing information component 412, and a fourth credentialing information component 414. It must be appreciated that though the computer executable aggregated credentialing information 216 is shown to comprise only four credentialing sub-components obtained from the credentialing information sources 402 as an example, however the aggregated credentialing information 216 in reality is obtained and generated from crowdsourced credentialing information sources 402 comprising of hundreds of or thousands of credentialing sources contained within the credentialing information sources 402. Each source in the credentialing information sources 402 provide a credentialing to the structured computer executable profile information or a portion of the computer executable profile information represented through a respective credentialing information component. For example, a credentialing source from the credentialing information sources 402 may provide credentialing to education component of the clinician personal information 212 contained within the structured initial computer executable profile information 208 such that the credentialing of the education may be represented through the first credentialing information component 408. Similarly, another credentialing source may provide credentialing to education component of the same clinician personal information 212 contained within the structured initial computer executable profile information 208 such that the credentialing of the education by the second source may be represented through the second credentialing information component 410. Similarly, a third credentialing source may provide credentialing to education component of the same clinician personal information 212 contained within the structured initial computer executable profile information 208 such that the credentialing of the education by the third source may be represented through the third credentialing information component 412. And, a fourth credentialing source may provide credentialing to education component of the same clinician personal information 212 contained within the structured initial computer executable profile information 208 such that the credentialing of the education by the fourth source may be represented through the fourth credentialing information component 414. In some example, such credentialing may be provided by the crowd of the credentialing information sources 402 in the form of several credentialing components for the education. In a similar manner, several other credentialing sources may provide credentialing of other components of the computer executable profile information.

The processing circuit 204 may generate the aggregated credentialing information 216 based on the first credentialing information component 408, the second credentialing information component 410, the third credentialing information component 412, and the fourth credentialing information component 414, and so on (referred to simply as credentialing information component 408-414).

The processing circuit 204 may facilitate aggregation of the credentialing information components 408-414 taken from or generated by the credentialing information sources 402 and apply rules to determine a cumulative or the aggregated credentialing information 216. The aggregated credentialing information 216 may be determined by the processing circuit 204 by using one or more of various algorithms or methods including without limitations such as simple averaging, weighted averaging, summation, mean, and the like and various other ways. In accordance with various embodiments herein, the aggregated credentialing information 216 as determined by the processing circuit 204 may be filtered for superfluous, erroneous, or fraudulent ratings or effects. The aggregated credentialing information 216 obtained by the processing circuit 204 may be published and used as a part of the computer executable profile information.

In an embodiment, the computer executable clinician personal information 212 may include such as clinician first name, clinician last name, medical specialty, treatment information, criminal background checks, and litigation information, and the computer executable profile fields may include a unique profile field for each of the clinician first name, clinician last name, medical specialty, treatment information, criminal background checks, and the litigation information.

In an embodiment, the computer executable aggregated credentialing information 216 may include the individual credentialing information components 408-414 such that a unique computer executable profile field is associated with each of the individual credentialing information components 408-414.

In an embodiment, the computer executable review information 214 comprises reviews from patients and peers such that a unique computer executable profile field is associated with each of the reviews from the patients and peers.

In an example, each of the individual credentialing information components 408-414 may include a computer executable clinician rating provided by the credentialing information sources 402.

In an example, the transmission and signaling of information from the different information sources 404 including the credentialing information sources 402 and the other information sources 406 to the database 206 may be enabled in one of the several ways as discussed below in conjunction with FIG. 7.

Figure 5:
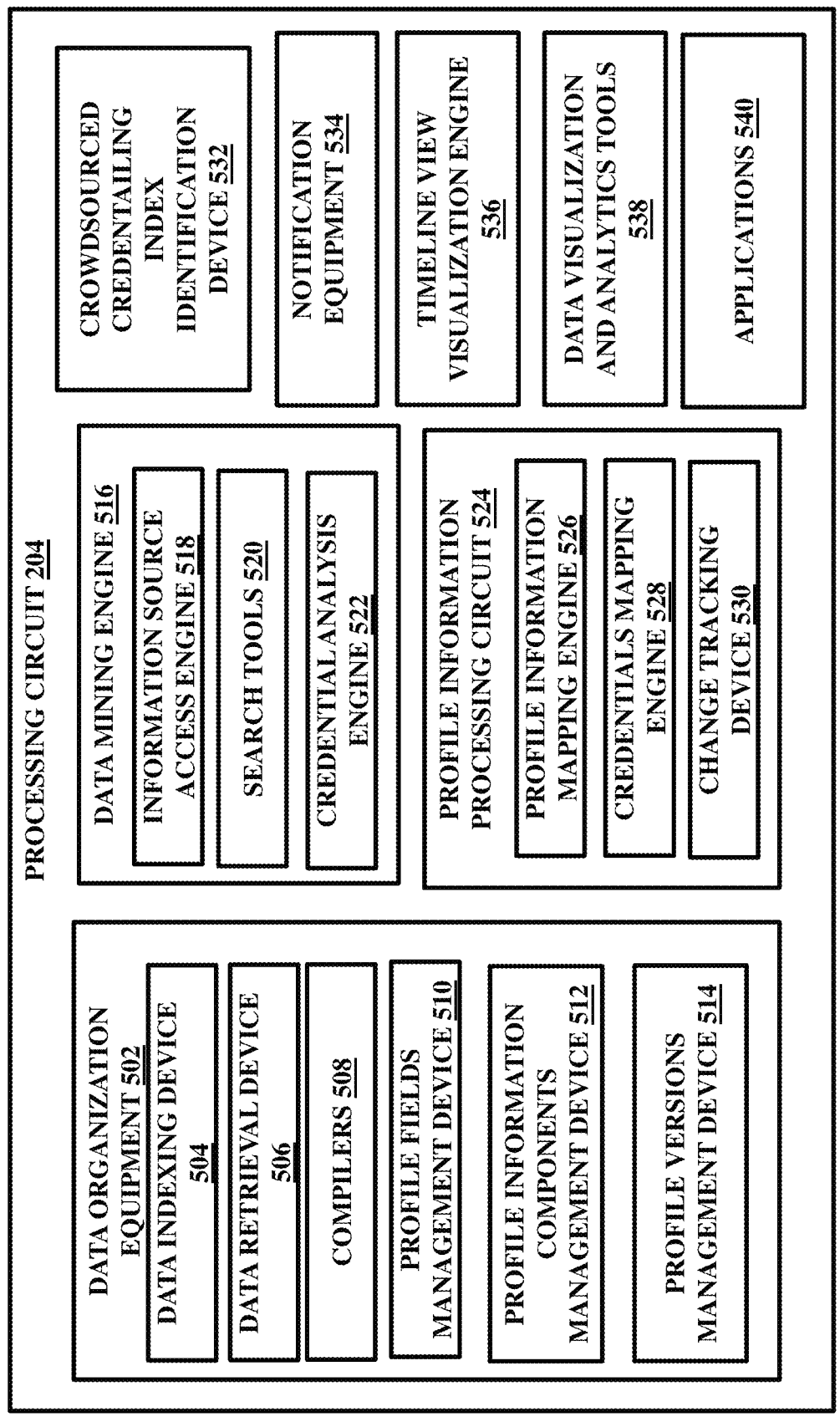
FIG. 5 illustrates various components of a processing circuit, in accordance with an embodiment herein.

FIG. 5, with reference to FIGS. 1 through 4, illustrates various components of the processing circuit 204 in accordance with an embodiment herein.

The processing circuit 204 may include a data organization equipment 502. The data organization equipment 502 may include a data indexing device 504, a data retrieval device 506, compilers 508, profile fields management device 510, profile information components management device 512, and profile versions management device 514. The data retrieval device 506 may facilitate retrieval of the computer executable profile information from the plurality of information sources 404 as discussed earlier. The data indexing device 504 may index various data pieces of the computer executable profile information in the cloud staging repositories 202 and/or within the database 206 for proper organization. The profile fields management device 510 may define the set of profile fields of the computer executable profile information for structuring of the computer executable profile information. The profile information components management device 512 may associate the profile information components with the profile fields for structuring the computer executable profile information. The profile versions management device 514 may generate different time-based versions of the computer executable profile information that may vary from one another based on the changes in the computer executable profile information as discussed above.

The processing circuit 204 may include the data mining engine 516. The data mining engine 516 may include information source access engine 518 that may access the plurality of information sources 404 as discussed above for creating the computer executable profile information. Once the information sources 404 are accessed, the data retrieval device 506 may be used to retrieve necessary data for the computer executable profile information from the information sources 404. In an embodiment, the information sources 404 may be identified and pre-defined. In an example, the processing circuit 204 may also identify new information sources using search tools 520. The data mining engine 516 may include credential analysis engine 522 that may be used to analyze reputation and review score of the credentialing sources 402 as discussed in conjunction with FIG. 4 to provide a weightage to the various credentialing components 408-414.

The processing circuit 204 may further include a profile information processing circuit 524 to perform various processing activities of the computer executable profile information. The processing activities may include pre-processing activities and post-processing activities as discussed elsewhere in the document without limitations. The profile information processing circuit 524 may include a profile information mapping engine 526 for mapping of the structured initial computer executable profile information with subsequent structured computer executable profile information to determine any changes in the structured computer executable profile information. The credentials mapping engine 528 may perform mapping of credentials within the initial computer executable profile information with credentials within the subsequent version of the computer executable profile information to identify any changes in credentialing of the computer executable profile information. The processing circuit 204 may include a change tracking device 530 to track any changes in the credentialing of the computer executable profile information or changes in the overall computer executable profile information or various components thereof. The changes in the computer executable profile information over time have been discussed earlier in the document without limitations.

The processing circuit 204 may further include a crowdsourced credentialing index identification device 532. The crowdsourced credentialing index identification device may use the aggregated credentialing information 216 to generate a crowdsourced credentialing index that is indicative of credentialing of the computer executable profile information from the plurality of credentialing sources 402. The more the crowdsourced credentialing index associated with the computer executable profile information, the more is the reliability and trustworthiness of the computer executable profile information. In some embodiments, the crowdsourced credentialing index may be associated with each of the versions of the computer executable profile information over time so that any change in the crowdsourced credentialing index over time may be indicative of a change in the reliability and trustworthiness of the computer executable profile information such that the change tracking device 530 may identify the change in the crowdsourced credentialing index and notify through notifications accordingly.

The processing circuit 402 may further include a notification equipment 534 to selectively generate the notifications and alerts either proactively every time the change is identified or as desired upon input through a query submitted to the processing circuit 204 by an external computer such as discussed elsewhere in the document.

In an example, the notification equipment may be communicatively connected with the processing circuit for generating the alerts indicative of a fraudulent profile when the crowdsourced credentialing index for the clinician profile based on the identified changes over time exceed a defined threshold. In an example, the notification equipment may be alternatively configured to generate the alerts indicative of the fraudulent profile when the changes are identified in the profile information components corresponding to any of the computer executable profile fields. In an example, the notification equipment may be alternatively configured to generate the alerts indicative of the fraudulent profile when the changes are identified in profile fields corresponding to the individual credentialing information components.

The processing circuit 204 may further include a timeline view visualization device 536 that may use the change identified by the change tracking device 530 along with the various versions of the computer executable profile information over time to provide a visualization through visualization tools such that a display of the visualization may present the changes in the various versions of the computer executable profile information over time through a timeline view. The timeline view may represent through visualization techniques the changes and various evolutions in the computer executable profile information over time.

Figure 6:
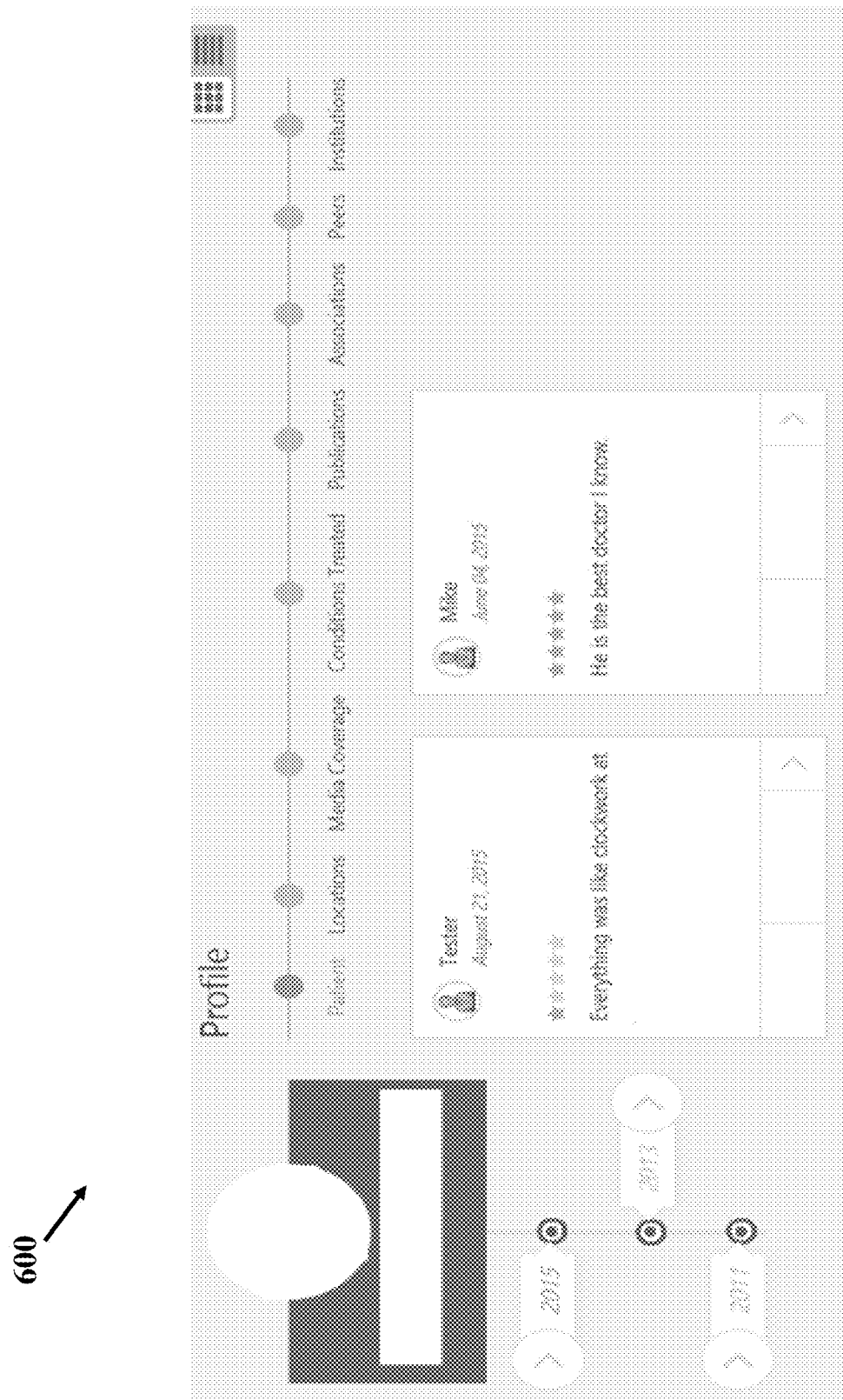
FIG. 6 illustrates visualization of an exemplary timeline view and a computer executable profile information, in accordance with an embodiment herein.

FIG. 6, with reference to FIGS. 1 through 5, illustrates visualization of an exemplary timeline view and the computer executable profile information in accordance with an embodiment herein. As shown, the processing circuit 204 presents three versions of the structured computer executable profile information as identified for the year 2015, year 2013, and year 2011. A user may click on any of the versions and accordingly can view a corresponding version of the structured computer executable profile information. In an embodiment, the user may note the changes in any two versions of the structured computer executable profile information on a user interface presented on a display unit. In an embodiment, when the user selects a specific year, the textual information corresponding to that year are formatted and structured to fit a profile window 600. In an embodiment, if the user changes a size of the profile window 600, the textual information is reformatted and relocated to an unobscured portion of the profile window.

Referring back to FIG. 5, the processing circuit 204 may utilize a set of data visualization and analytics tools 538 to process various visualizations tasks and generate the timeline views across different versions of the structured computer executable profile information. The visualization and presentation may be customized to give each user a customized experience based on his requirements and based on the type of changes tracked by the change tracking device 530. For example, the presentation of the computer executable profile information or the structured computer executable profile information and various versions or components thereof and the changes tracked by the processing circuit 204 may be created for a wide variety of uses with specific customization for each of the uses done accordingly to create a customized view for each type of use and each type of user.

In an example, the processing circuit 204 may execute a plurality of applications 540 on top of various processing activities. The applications 540 may for example include electronic health record auditor, clinician profiler, electronic health record network, prediction tools, predictive patient outreach, and the like without limitations.

In an example, before presentation of the structured computer executable profile information and the changes on the display unit through the visualization techniques, the processing circuit 204 may perform various processing activities as discussed in conjunction with FIG. 1 above. The processing activities may further include various pre-processing and post-processing activities that may be performed by the processing circuit 204. This may include for example harmonization of data components to create a consistent view of the various data components and the fields information components of the computer executable profile information.

In an example, an embodiment herein allows revision history and storage of change tracking of data longitudinally over time. In an example, an embodiment herein allows visualizations showing how data changed over time (longitudinally). In an example, an embodiment herein alerts and notification when any information changes (and show via email/SMS/etc.). In an example, an embodiment herein allows alerts and notifications based on search criteria (e.g. watch for specific words and alert on them). In an embodiment, the alert notifications may be sent to a user's computer over a wireless channel, and the user's computer retrieves the updated profile, including the information change, when it is connected to the Internet. In an example, an embodiment herein provides different views of data to different roles of users (e.g. show patients what they care about, show hospitals what they care about, etc.).

In an example, an embodiment herein provides a time-dependent longitudinal view of computer executable profiles. The invention provides a longitudinal view of what the computer executable profile look like on January 1st vs. what it looks like today for example. An embodiment herein allows identifying difference between credentials in January and credentials today for example. For example, a user may want to do a 100 million dollar clinical trial and he may use a clinician as an investigator in January when everything was fine but later he may find a risk of fraud. If the user does not know that something has changed immediately there is a huge risk. An embodiment herein allows mitigating this risk through longitudinal views of the computer executable profile over time.

In an example, the transmission and signaling of information across different entities such as the cloud staging repositories 202, the processing circuit 204, and the database 206 may be enabled in one of the several ways. In an example, the information may be pulled automatically from the information sources through pre-defined and customizable Application Programming Interfaces (APIs) designed for specific information sources and transmitted into the database 206 and the cloud staging repositories 202 through processing instructions performed by the processing circuit 204. In an example, the APIs may be third party APIs that may be configured to interact with systems disclosed herein. In an example, the information may be pulled automatically from the information sources through scraping scripts, ATOM feeds, and RSS feeds so that the pulled information may be passed into the database 206 and the cloud staging repositories 202 by the processing circuit 204 upon execution of the processing instructions. In an example, the information may be pulled in manually from the information sources through ad hoc requests such as manual file uploads. The files may be defined in a format so that these are ingestible into the database 206 and the cloud staging repositories 202 upon executing predefined processing instructions executable by the processing circuit 204.

Figure 7:
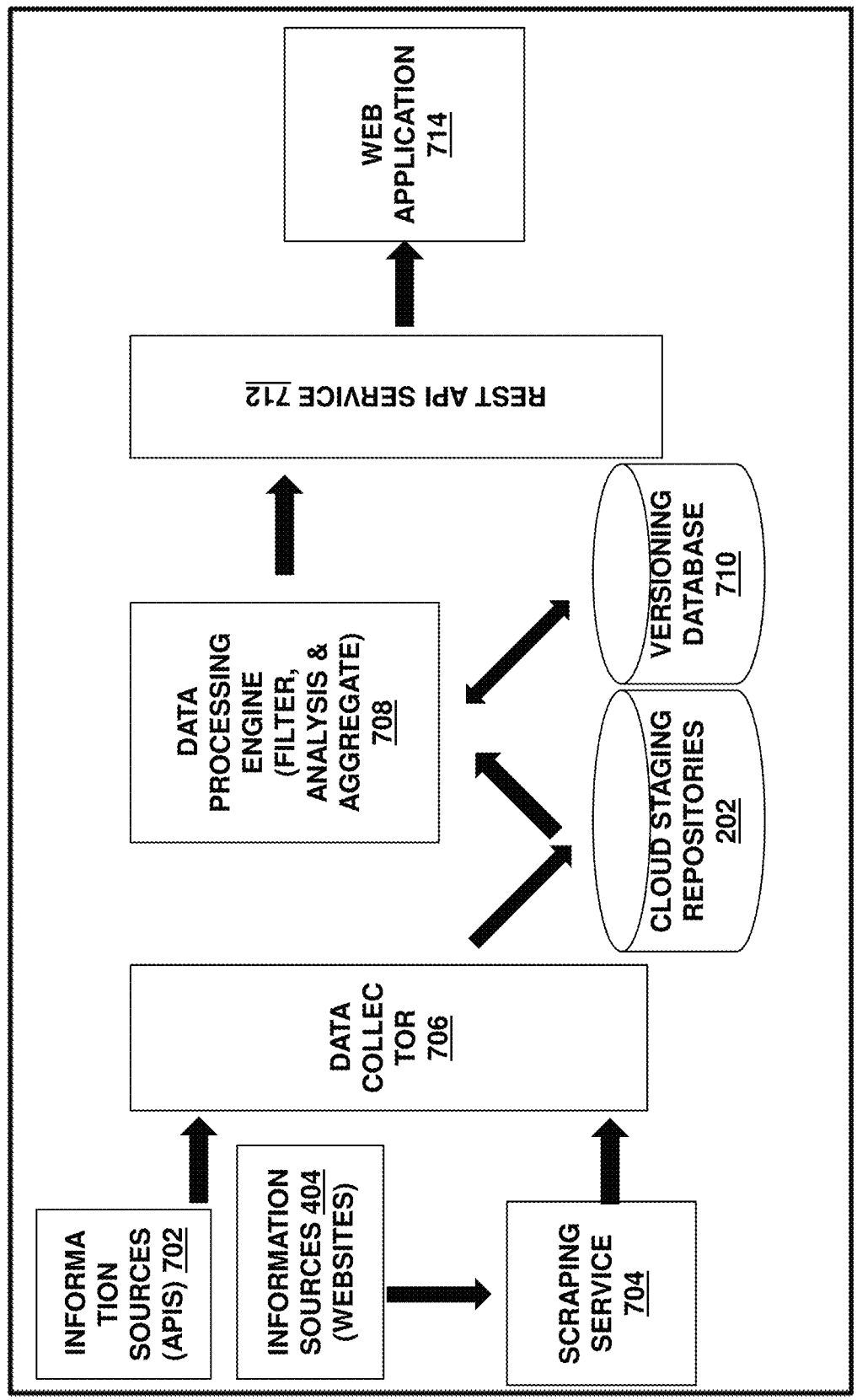
FIG. 7 is a schematic architecture diagram illustrating transmission and signaling of information across various components, in accordance with an embodiment herein.

FIG. 7, with reference to FIGS. 1 through 6, for example illustrates an architecture diagram illustrating the transmission and signaling of information across various components. The information sources 404 may be associated with APIs 702 that may be used to collect, extract and receive data by a data collector 706 in an example. In an example, the data collector 706 may obtain the data from the information sources 404 through a scraping device 704. The scraping device 704 may perform scraping operations for the data collector 706 to extract the scraped data. In some embodiments, the data collector 706 may utilize other devices as well to receive the data from the information sources 404 using modes such as not limited to ATOM feeds, RSS feeds etc. The data collector may transmit the data to the cloud staging repositories 202. The processing circuit 204 or a data processing engine 708 included within or communicatively coupled to the processing circuit 204 may receive the data from the cloud staging repositories 202. The processed data may be stored in a versioning database 710. The versioning database 710 for example may store different versions of the computer executable profiles over time. A REST API service 712 may allow transmission of the processed data or the computer executable profiles or changes in the computer executable profiles to a web application 714 where a signal representing the transmitted data or the computer executable profiles or changes in the computer executable profiles may be converted into display images viewable through a web browser.

The embodiments herein may be embodied as a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon. Such non-transitory computer readable storage media can be any available media that can be accessed by a special purpose device, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose device to perform a certain function or group of functions. Computer-executable instructions also include program modules that are executed by computers in stand-alone or network environments. Generally, program modules include routines, programs, components, data structures, objects, and the functions inherent in the design of special-purpose devices, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, map, union, variant, set, graph, tree, node, and an object, which may be stored and retrieved by computer memory and may be managed by processors, compilers, and other computer hardware components. The data paths can be configured as part of a special computer CPU that performs operations and calculations as instructed by the computer logic instructions. The data paths could include digital electronic circuits, multipliers, registers, and buses capable of performing data processing operations and arithmetic operations (e.g., Add, Subtract etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, and triggers.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor, and may be configured, for example, as a kiosk.

The embodiments herein can include both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 8:
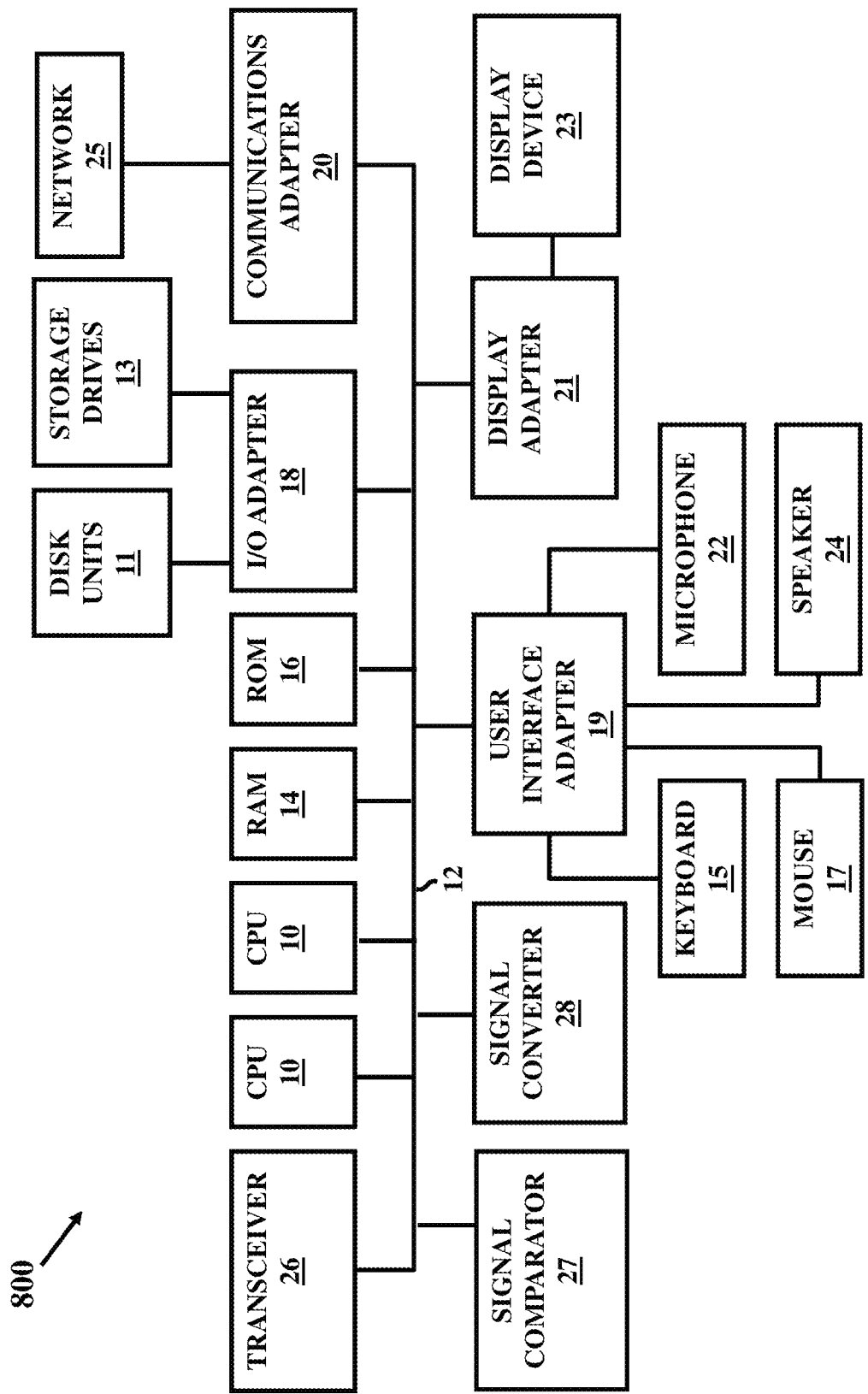
FIG. 8 illustrates a computer system that may be used in accordance with the embodiments herein.

A representative hardware environment for practicing the embodiments herein is depicted in FIG. 8, with reference to FIGS. 1 through 7. This schematic drawing illustrates a hardware configuration of an information handling/computer system 800 in accordance with the embodiments herein. The system 800 comprises at least one processing device 10. The special-purpose CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system 800. The system 800 can read the inventive instructions on the program storage devices and follow these instructions to execute the methodology of the embodiments herein. The system 800 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

Figure 9:
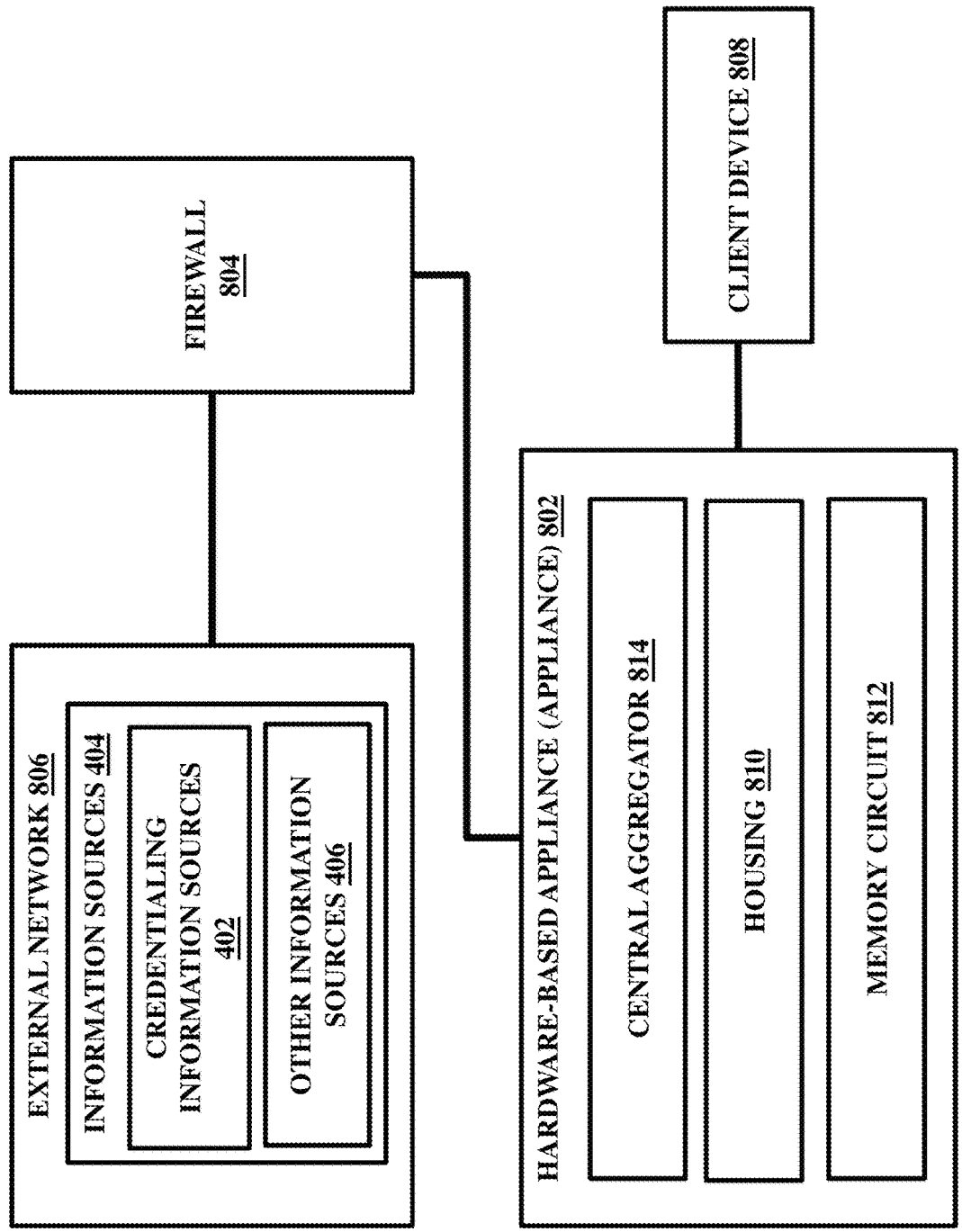
FIG. 9 is a schematic diagram illustrating a hardware-based appliance (appliance) stored behind a firewall and communicatively and operatively connected with an external network and a client device, in accordance with the embodiments herein.

FIG. 9, with reference to FIGS. 1 through 8, illustrates a schematic diagram of a hardware-based appliance (appliance) 902 stored behind a firewall 904 and communicatively and operatively connected with an external network 906 and a client device 908, in accordance with the embodiments herein. The appliance 902 may include a housing 910 for storing necessary hardware equipment and circuitry. The appliance 902 may include a memory circuit 912 for maintaining the database 206 to store the initial computer executable profile information and the aggregated credentialing information obtained from the credentialing information sources 402 from the external network 906.

In an example, the appliance 902 may include a central aggregator 914. The central aggregator 914 may allow access by the client device 908 to the database 206 or a portion thereof privately along with an access of a bundle of other information houses through a secured and privately owned single subscription. For example, the client device 808 may already have an access to ten other databases. The client device 908 may additionally be provided access to the database 206 for accessing the structured initial computer executable profile information and the structured second computer executable profile information along with the ten other databases by the central aggregator 914. The central aggregator 914 may aggregate content stored in the database 206 with content of the ten other databases so that the client device 908 gets a feel of accessing only one single database through a single access point. As shown in FIG. 9, the appliance 902 may be stored behind the firewall 904 and the firewall 904 may be configured so as to allow communication among the appliance 902, the client device 908, and the external network 906.

In an example, the appliance 902 may be packaged as a hardware device or a kiosk or a standalone product to be available as ready to install in an environment. A user may connect the appliance 902 to a power source and install or configure appliance settings by connecting it communicatively with a server. Once the appliance 902 is installed, the appliance 902 may be ready to use.

Figure 10:
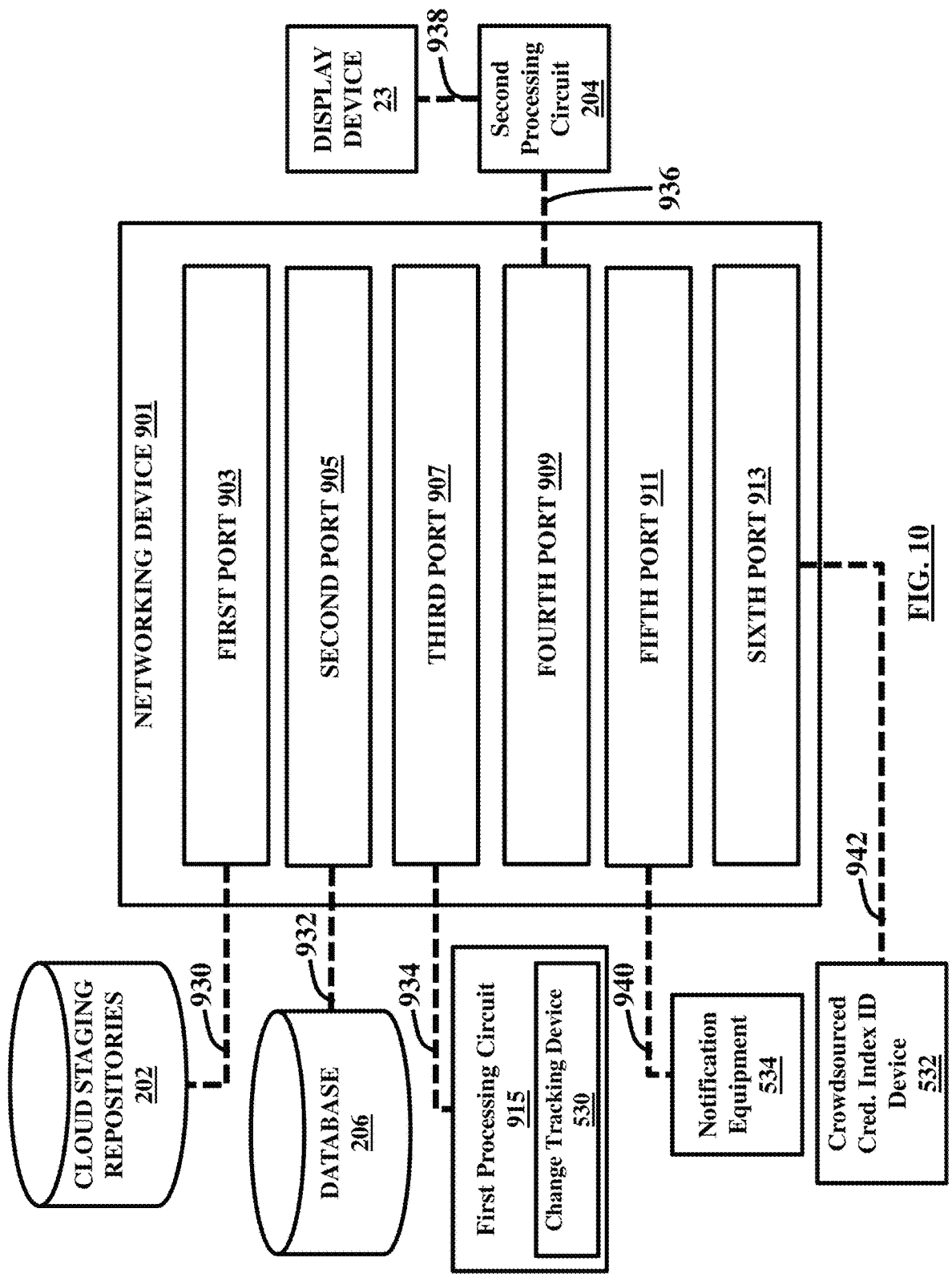
FIG. 10 is a schematic diagram of a networking device and linked components according to an embodiment herein.

FIG. 10, with reference to FIGS. 1 through 9, illustrates a networking device 901 for storing tracked changes in a computer executable clinician web-based profile according to an embodiment herein. The networking device 901 comprises a first signal port 903 linking a first communication signal 930 to a plurality of cloud staging repositories 202 that store computer executable profile information as obtained from a plurality of information sources in unstructured form; a second signal port 905 linking a second communication signal 932 to a database 206 for storing structured initial computer executable profile information, wherein the structured initial computer executable profile information includes computer executable clinician personal information, computer executable review information, and computer executable aggregated credentialing information, wherein the computer executable profile information is aggregated from the plurality of information sources comprising a plurality of credentialing information sources such that the computer executable aggregated credentialing information is generated based on individual credentialing information components retrieved from the plurality of credentialing information sources.

The networking device 901 further comprises a third signal port 907 linking a third communication signal 934 to a first processing circuit 915 that executes logic instructions comprising a set of computer executable notification rules to selectively (1) generate default notifications corresponding to changes in the structured initial computer executable profile information upon identification of such changes, and (2) generate notifications corresponding to the changes in the structured initial computer executable profile information over a defined time period as and when requested by an external computer through a search query; and a fourth signal port 909 linking a fourth communication signal 936 to a second processing circuit 204 to split the computer executable profile information into constituent data types; define a plurality of computer executable profile fields and corresponding profile information components for each of the plurality of computer executable profile fields; access the plurality of credentialing information sources after a defined interval of time to obtain the individual credentialing information components as indicated at a later time; generate structured second computer executable profile information based on the obtained individual credentialing information components from the plurality of credentialing information sources as indicated at the later time; map the structured initial computer executable profile information with the structured second computer executable profile information to identify the changes in the profile information components corresponding to the computer executable profile fields, wherein the changes are indicative of a change in reliability of credentialing of the computer executable clinician profile over time; execute the set of computer executable notification rules to generate the notifications; determine a crowdsourced credentialing index for the clinician profile based on the changes over time obtained from the mapping of the structured initial computer executable profile information and the structured second computer executable profile information; generate an electric signal comprising data signifying the structured second computer executable profile information and changes in the structured initial computer executable profile information; transmit the electric signal in a network 25 comprising a plurality of communicatively linked data communication devices; convert the electric signal into a plurality of pixels 938; and display 23 the plurality of pixels 938 on a display 23 unit to indicate timeline views of the structured initial computer executable profile information and the changes based on the computer executable notification rules.

The networking device 901 further comprises a fifth signal port 911 linking a fifth communication signal 940 to a notification equipment 534 communicatively connected with the first processing circuit 915 for generating an alert indicative of a fraudulent profile when the crowdsourced credentialing index for the clinician profile based on the changes over time exceed a defined threshold. The notification equipment 534 is configured to generate the alert indicative of the fraudulent profile when the changes are identified in the profile information components corresponding to any of the computer executable profile fields. The notification equipment 534 is configured to generate the alert indicative of the fraudulent profile when the changes are identified in profile fields corresponding to the individual credentialing information components. The first processing circuit 915 further comprises a timeline view visualization device, wherein the timeline view visualization device uses the identified changes along with time instances of the structured initial computer executable profile information over time to provide a visualization such that a display 23 of the visualization presents the identified changes and the time instances of the structured initial computer executable profile information over time in a timeline view longitudinally. The first processing circuit 915 further comprises a change tracking device 530 to track the changes in the credentialing of the structured initial computer executable profile information. The networking device 901 further comprises a sixth signal port 913 linking a sixth communication signal 942 to a crowdsourced credentialing index identification device that uses the aggregated credentialing information to generate the crowdsourced credentialing index indicative of credentialing of the structured initial computer executable profile information from the plurality of credentialing sources.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodi-

I claim:

1. A computer-implemented method for tracking change over a period of time in a computer executable profile associated with a registered clinician, said method comprising:
retrieving, by a processing circuit, said computer executable profile information for said registered clinician, wherein said computer executable profile information includes computer executable clinician personal information, computer executable review information, and computer executable aggregated credentialing information obtained based on individual credentialing information components retrieved from a plurality of credentialing information sources;
staging, by a processing circuit, said computer executable profile information in one or more cloud staging repositories;
splitting, by a processing circuit, said computer executable profile information into constituent data types, wherein said constituent data types represent two or more fragments of said computer executable profile information;
defining, by said processing circuit, a plurality of computer executable profile fields and corresponding profile information components for each of said plurality of computer executable profile fields that are readable by said processing circuit for mapping;
storing, by said processing circuit, said computer executable profile information including said computer executable profile fields and said corresponding profile information components as structured initial computer executable profile information in a database communicatively connected with said processing circuit;
accessing, by said processing circuit, said plurality of credentialing information sources after a defined interval of time to obtain said individual credentialing information components as indicated at a later time;
retrieving, by said processing circuit, structured second computer executable profile information based on said obtained individual credentialing information components from said plurality of credentialing information sources as indicated at said later time;
mapping, by said processing circuit, said structured initial computer executable profile information with said structured second computer executable profile information to identify changes in said profile information components corresponding to said computer executable profile fields, wherein said changes are indicative of reliability of credentialing of said computer executable profile over time;
defining, by said processing circuit, a set of computer executable notification rules to selectively:
generate notifications corresponding to changes between said structured initial computer executable profile information and said structured second computer executable profile information upon identification of such changes;
generate notifications corresponding to said changes between said structured initial computer executable profile information and said structured second computer executable profile information over a defined time period as and when requested by a user computer, communicatively connected with said processing circuit, through a search query submitted to said processing circuit;
determining, by said processing circuit, a crowdsourced credentialing index for said computer executable profile based on said changes over time obtained from said mapping of said structured initial computer executable profile information and said structured second computer executable profile information;
generating, by said processing circuit, an electric signal comprising data signifying said changes in said structured initial computer executable profile information;
transmitting, by said processing circuit, said electric signal from said processing circuit, in a network comprising a plurality of communicatively linked data communication devices;
converting, by said processing circuit, said electric signal into a plurality of pixels; and
displaying, by said processing circuit, said plurality of pixels on a display unit to indicate timeline views of said structured second computer executable profile information and said changes based on said computer executable notification rules.

2. The method of claim 1, wherein said computer executable clinician personal information comprising clinician first name, clinician last name, medical specialty, treatment information, criminal background checks, and litigation information; and said computer executable profile fields comprising a unique profile field for each of said clinician first name, clinician last name, medical specialty, treatment information, criminal background checks, and said litigation information.

3. The method of claim 1, wherein said computer executable aggregated credentialing information comprises said individual credentialing information components such that a unique computer executable profile field is associated with each of said individual credentialing information components.

4. The method of claim 1, wherein said computer executable review information comprises reviews from patients and peers such that a unique computer executable profile field is associated with each of said reviews from said patients and peers.

5. The method of claim 1 further comprising generating, by said processing circuit, an alert indicative of a clinician fraud when said crowdsourced credentialing index for said clinician profile based on said changes over time drops below a defined threshold.

6. The method of claim 1 further comprising generating, by said processing circuit, an alert indicative of a clinician fraud when said changes are identified in said profile information components corresponding to any of said computer executable profile fields.

7. The method of claim 1 further comprising generating, by said processing circuit, an alert indicative of a clinician fraud when said changes are identified in profile fields corresponding to said individual credentialing information components.

8. The method of claim 1, wherein each of said individual credentialing information components comprises a computer executable clinician rating provided by said credentialing information sources.

9. A networking device for storing tracked changes in a computer executable clinician web-based profile, said networking device comprising:
a first signal port linking a first communication signal to a plurality of cloud staging repositories that store computer executable profile information as obtained from a plurality of information sources in unstructured form;

a second signal port linking a second communication signal to a database for storing structured initial computer executable profile information, wherein said structured initial computer executable profile information includes computer executable clinician personal information, computer executable review information, and computer executable aggregated credentialing information, wherein said computer executable profile information is aggregated from said plurality of information sources comprising a plurality of credentialing information sources such that said computer executable aggregated credentialing information is generated based on individual credentialing information components retrieved from said plurality of credentialing information sources;

a third signal port linking a third communication signal to a first processing circuit that executes logic instructions comprising a set of computer executable notification rules to selectively (1) generate default notifications corresponding to changes in said structured initial computer executable profile information upon identification of such changes, and (2) generate notifications corresponding to said changes in said structured initial computer executable profile information over a defined time period as and when requested by an external computer through a search query;

a fourth signal port linking a fourth communication signal to a second processing circuit to:
  split said computer executable profile information into constituent data types;
  define a plurality of computer executable profile fields and corresponding profile information components for each of said plurality of computer executable profile fields;
  access said plurality of credentialing information sources after a defined interval of time to obtain said individual credentialing information components as indicated at a later time;
  generate structured second computer executable profile information based on said obtained individual credentialing information components from said plurality of credentialing information sources as indicated at said later time;
  map said structured initial computer executable profile information with said structured second computer executable profile information to identify said changes in said profile information components corresponding to said computer executable profile fields, wherein said changes are indicative of a change in reliability of credentialing of said computer executable clinician profile over time;
  execute said set of computer executable notification rules to generate said notifications;
  determine a crowdsourced credentialing index for said clinician profile based on said changes over time obtained from said mapping of said structured initial computer executable profile information and said structured second computer executable profile information;
  generate an electric signal comprising data signifying said structured second computer executable profile information and changes in said structured initial computer executable profile information;
  transmit said electric signal, in a network comprising a plurality of communicatively linked data communication devices;
  convert said electric signal into a plurality of pixels; and
  display said plurality of pixels on a display unit to indicate timeline views of said structured initial computer executable profile information and said changes based on said computer executable notification rules; and a hardware-based appliance located behind a firewall and comprising:
  a housing for storing hardware equipment and circuitry including said first processing circuit,
  a memory circuit for maintaining said database to store said structured initial computer executable profile information obtained from said plurality of information sources, and
  a processing circuit to allow said first signal port, said second signal port, said third signal port, and said fourth signal port to perform their respective tasks.

10. The networking device of claim 9, further comprising a fifth signal port linking a fifth communication signal to a notification equipment communicatively connected with said first processing circuit for generating an alert indicative of a fraudulent profile when said crowdsourced credentialing index for said clinician profile based on said changes over time exceed a defined threshold.

11. The networking device of claim 10, wherein said notification equipment is configured to generate said alert indicative of said fraudulent profile when said changes are identified in said profile information components corresponding to any of said computer executable profile fields.

12. The networking device of claim 11, wherein said notification equipment is configured to generate said alert indicative of said fraudulent profile when said changes are identified in profile fields corresponding to said individual credentialing information components.

13. The networking device of claim 9, wherein said first processing circuit further comprises a timeline view visualization device, wherein said timeline view visualization device uses said identified changes along with time instances of said structured initial computer executable profile information over time to provide a visualization such that a display of said visualization presents said identified changes and said time instances of said structured initial computer executable profile information over time in a timeline view longitudinally.

14. The networking device of claim 9, wherein said first processing circuit further comprising a change tracking device to track said changes in said credentialing of said structured initial computer executable profile information.

15. The networking device of claim 9, further comprising a sixth signal port linking a sixth communication signal to a crowdsourced credentialing index identification device that uses said aggregated credentialing information to generate said crowdsourced credentialing index indicative of credentialing of said structured initial computer executable profile information from said plurality of credentialing sources.

* * * * *